(12) United States Patent
Stein et al.

(10) Patent No.: US 8,382,475 B2
(45) Date of Patent: Feb. 26, 2013

(54) METHOD AND DEVICE FOR CONTROLLING THE POSITION OF BORE BUSHINGS

(75) Inventors: Wolfram Stein, Heidelberg (DE); Florian Schober, Zurich (CH); Leonhard Blümcke, Graben-Newdorf (DE)

(73) Assignee: MED3D GmbH (DE)

( * ) Notice: Subject to any disclaimer, the term of this patent is extended or adjusted under 35 U.S.C. 154(b) by 1021 days.

(21) Appl. No.: 10/547,108

(22) PCT Filed: Feb. 23, 2004

(86) PCT No.: PCT/EP2004/001750
§ 371 (c)(1),
(2), (4) Date: Nov. 18, 2005

(87) PCT Pub. No.: WO2004/076106
PCT Pub. Date: Sep. 10, 2004

(65) Prior Publication Data
US 2006/0105291 A1   May 18, 2006

(30) Foreign Application Priority Data
Feb. 28, 2003   (DE) .................................. 103 09 992

(51) Int. Cl.
*A61C 3/00*   (2006.01)
(52) U.S. Cl. .......................................................... 433/75
(58) Field of Classification Search ............... 433/75, 433/76, 213, 214, 215, 72; 33/286, 513–514; 600/589–590; 29/407.05, 407.09, 407.1
See application file for complete search history.

(56) References Cited

U.S. PATENT DOCUMENTS

| 2,545,249 | A | * | 3/1951 | Ackerman .................. 433/3 |
| 3,344,525 | A | * | 10/1967 | Harris ...................... 433/50 |
| 4,171,570 | A | * | 10/1979 | Seldin ..................... 433/73 |
| 4,557,599 | A | * | 12/1985 | Zimring ................. 356/243.1 |
| 4,840,564 | A | * | 6/1989 | Segal ..................... 433/72 |
| 5,015,183 | A |   | 5/1991 | Fenick .................... 433/76 |
| 5,133,660 | A |   | 7/1992 | Fenick .................... 433/76 |
| 5,222,892 | A |   | 6/1993 | Perry ..................... 433/75 |
| 5,368,478 | A | * | 11/1994 | Andreiko et al. .......... 433/24 |
| 5,431,562 | A | * | 7/1995 | Andreiko et al. .......... 433/24 |

(Continued)

FOREIGN PATENT DOCUMENTS

DE   41 25 894 A1   2/1992
FR   78036   5/1962

(Continued)

OTHER PUBLICATIONS

International Search Report PCT/EP2004/001750 dated Jun. 16, 2004.

*Primary Examiner* — Heidi M Eide
(74) *Attorney, Agent, or Firm* — Ostrolenk Faber LLP

(57) ABSTRACT

A method and a device for the simplified inspection of the compatibility of the positions of bore bushings in a drilling template with respect to the positions in a predetermined plan in a computer model. The position parameters are detected by a measuring device which is arranged at distance from the bore bushings. The position parameters are transferred to a measurement plane on a reference seat. The drilling template is held to the reference seat at at least one of a predetermined orientation or a predetermined distance from the measurement plane.

19 Claims, 4 Drawing Sheets

U.S. PATENT DOCUMENTS

| | | | | |
|---|---|---|---|---|
| 5,562,448 A | * | 10/1996 | Mushabac | 433/215 |
| 5,571,109 A | * | 11/1996 | Bertagnoli | 606/86 A |
| 5,725,376 A | * | 3/1998 | Poirier | 433/172 |
| 5,741,133 A | * | 4/1998 | Gordils et al. | 433/76 |
| 5,967,777 A | * | 10/1999 | Klein et al. | 433/75 |
| 6,018,562 A | * | 1/2000 | Willson | 378/9 |
| 2001/0038705 A1 | * | 11/2001 | Rubbert et al. | 382/128 |
| 2001/0053510 A1 | * | 12/2001 | Ranalli | 433/51 |
| 2002/0072028 A1 | * | 6/2002 | Taub et al. | 433/24 |
| 2002/0160337 A1 | * | 10/2002 | Klein et al. | 433/213 |

FOREIGN PATENT DOCUMENTS

| | | |
|---|---|---|
| FR | 2 706 281 | 12/1994 |
| FR | 2 778 457 | 11/1999 |
| WO | WO 99/32045 | 7/1999 |

\* cited by examiner

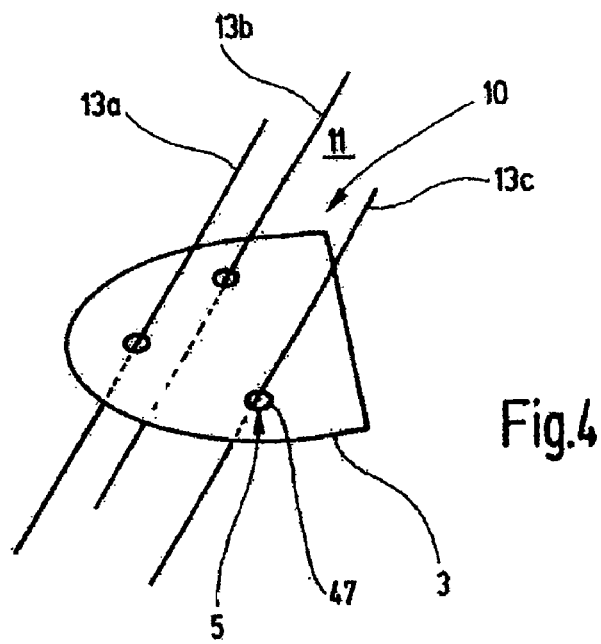
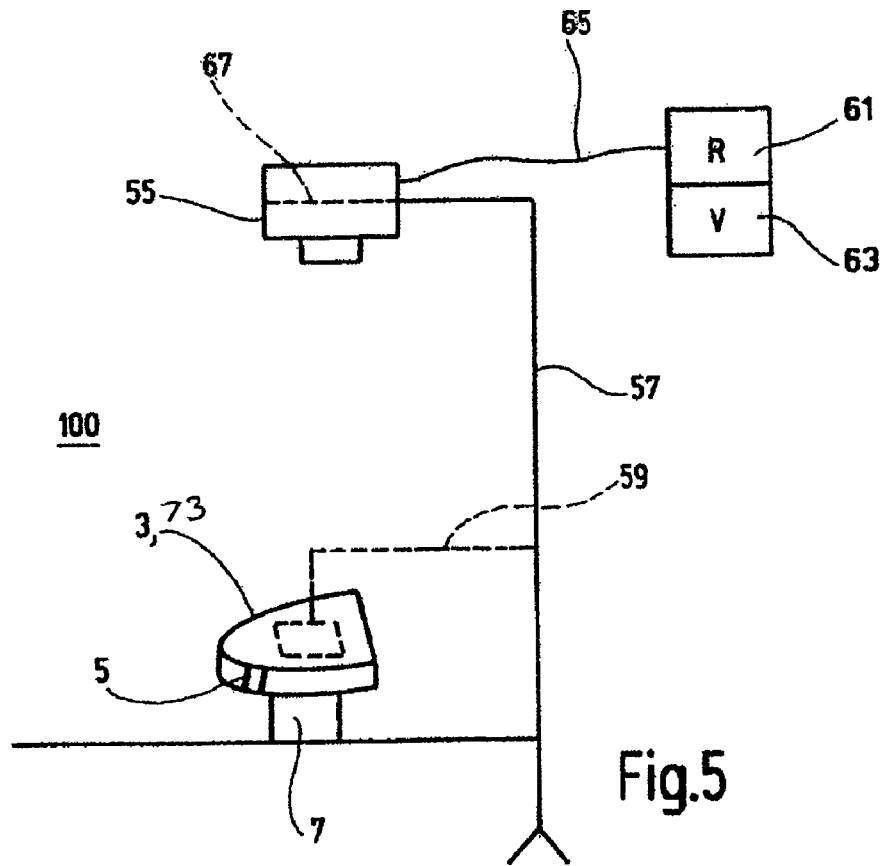

METHOD AND DEVICE FOR CONTROLLING THE POSITION OF BORE BUSHINGS

CROSS REFERENCE TO RELATED APPLICATION

The present application is a 35 U.S.C. §§371 national phase conversion of PCT/EP2004/001750, filed 2 Feb. 2004, which claims priority of German Application No. 103 09 992.1, filed 28 Feb. 2003. The PCT International Application was published in the German language.

BACKGROUND OF THE INVENTION

The invention relates to a method and a device for controlling the position of bore bushings in drilling templates which are used in the field of tooth implantation and serve to guide a drill which is used to create bores in a patient's jaw, for anchoring implants in these.

Drilling templates of this type are generally produced in the following way: First, a dentist takes an impression of a patient's jaw. The impression is used to produce a plaster model for creating a bite splint. The latter is worn by the patient while his jaw is recorded by computed tomography in order to permit a three-dimensional implant plan. To ensure that the plan can be transposed back to the patient, the drilling template typically contains registration markings. This plan ensures that the implants are disposed in the jaw bone such that, when creating the required bores for the implants, no nerves are damaged and there is no perforation of the paranasal sinuses. After establishing the course and arrangement of the drill channels and the drilling depth in the jaw bone, bore bushings are introduced into the bite splint. These preferably are made of titanium and are arranged such that they can be used to guide a drill with which the planned drill channels can be formed in the jaw. The angle disposition of the bore bushings is used to allow the drill channel to be formed at the desired orientation in the jaw bone. The drilling depth is fixed by the bore bushing edge which serves as an abutment for the drill and which surrounds the bushing inlet into which a drill is later inserted.

The bite splint which is provided with the bore bushings, and which now serves as a drilling template, is fitted in a patient who is to receive one or more implants. The bore bushings fixed in the bite splint or drilling template now act as a mechanical guide for the operator, and as an abutment for a drill with which holes are formed in the jaw in order to receive implants.

It has been found that, when introducing bore bushings into the bite splint, i.e. when producing the drilling template, deviations from the plan may arise in the positions of the bore bushings, e.g. as a result of human operating errors. Moreover, the bore bushings may be incorrectly axially introduced wrongly into the bite splint serving as the drilling template. The operator may be able to notice obvious errors from the arrangement of the bore bushings and by comparison with the images created by means of computed tomography. But, of course, not all errors can be picked up in this way, and so patients are endangered to the extent that the orientation of the bores formed in the jaw for the implants and the depth of the bores are sometimes determined incorrectly.

In the text below, "position" is understood, in each case with respect to a defined coordinate system, as the parameter values of the 6 degrees of freedom of a rigid object in three-dimensional space.

In a rotationally symmetrical bushing, the position is accordingly described unambiguously by 5 parameters.

A derived position parameter is obtained by conversion from parameter values of another coordinate system or by projection of the parameter values into a new coordinate system.

The terms "angle position and/or axial position" are used here synonymously for position parameters or for a subset of position parameters.

SUMMARY OF THE INVENTION

The object of the invention is therefore to make available a method and a device for simple control of the position of bore bushings fitted into a drilling template.

To achieve this object, in a proposed method, some of the position parameters or of the derived position parameters of the bore bushings in the drilling template are determined. In this case, the positions are measured at a distance from the drilling template, in particular to permit a high level of measurement accuracy and also a simple measurement.

In a particularly preferred method measurement takes place in a measurement plane assigned a reference seat. A reference seat holds the drilling template in a defined position in relation to the measurement plane, enable detecting the (derived) position parameters of the bore bushings.

An embodiment of the method is also preferred in which measurement pins are guided through the bore bushings, and the contact points of the measurement pins with the measurement plane are recorded. By comparing the contact points with reference points which lie in the measurement plane, it is possible to ascertain whether the bore bushings have been inserted correctly into the drilling template.

In a preferred embodiment of the method, the measurement pins are provided with measurement points in order to be able to ascertain whether those ends of the bore bushing serving as abutments are arranged in the correct axial position. If, for example, the measurement points are designed as abutments, the measurement pins may not reach the measurement plane if the bore bushings have been fitted too high. Thus, the operator can readily ascertain that the bore bushing is arranged in an incorrect axial position. If the bore bushing has been inserted too deep into the drilling template, this too can be readily seen by a practitioner from the measurement points on the measurement pins.

In a modified embodiment of the method, measurement pins are inserted into the bore bushings, and the distance of the ends of the measurement pins from one another and from a reference point is measured. The measurement is here carried out at a distance from the bore bushings so that, in the event of an incorrect angular disposition, the deviations can be better detected.

In a preferred embodiment of the method, the length of the measurement pins is predefined or a measurement point is fixed on them. If the ends of the measurement pins or their measurement points are not situated in a plane, it can be ascertained from this that the axial position of one or more bore bushings is not correct.

In a modified embodiment of the method, some of the position parameters or derived position parameters of the bore bushings are recorded by means of a camera or a flatbed or laser scanner. The measurement plane then coincides with the image plane of the camera.

Further embodiments of methods are disclosed.

To achieve the object of the invention, a device records some of the position parameters or derived position parameters of the bore bushings in a drilling template and records them at a distance from these bore bushings. This device enables the parameters to be recorded without disturbing the bore bushings or the drilling template.

A device is preferred in which a measurement plane is provided within which the (derived) position parameters are recorded. In this way, it is easily possible to record the (derived) position parameters with one measurement.

In a preferred illustrative embodiment of the device, the measurement plane is assigned a reference seat which holds the drilling template in a predetermined orientation and/or at a predeterminable distance with respect to the measurement plane. It is thus easily possible to guide measurement pins through the bore bushings and to compare their contact points with reference points in the measurement plane. The correct arrangement of the bore bushings can thus be recorded without any problems.

In another device of the kind in question here, measurement pins are guided through the bore bushings, and the distance of these measurement pins from one another and from a reference point is measured on these at a distance from the bore bushings, in order to record some of the position parameters or of the derived position parameters of the bore bushings. Here too, it is easily possible to check the positioning of the bore bushings.

Finally, an embodiment of the device is preferred which is characterized in that a camera is provided. This records some of the (derived) position parameters of the bore bushings in a simple manner.

Further illustrative embodiments of the various devices are disclosed.

BRIEF DESCRIPTION OF THE DRAWINGS

The invention is explained in more detail below with reference to the drawings, in which:

FIG. 4 shows a further illustrative embodiment of a device for controlling the position of bore bushings, and FIG. 5 shows a further illustrative embodiment of such a device.

DESCRIPTION OF PREFERRED EMBODIMENTS

Figure 1:
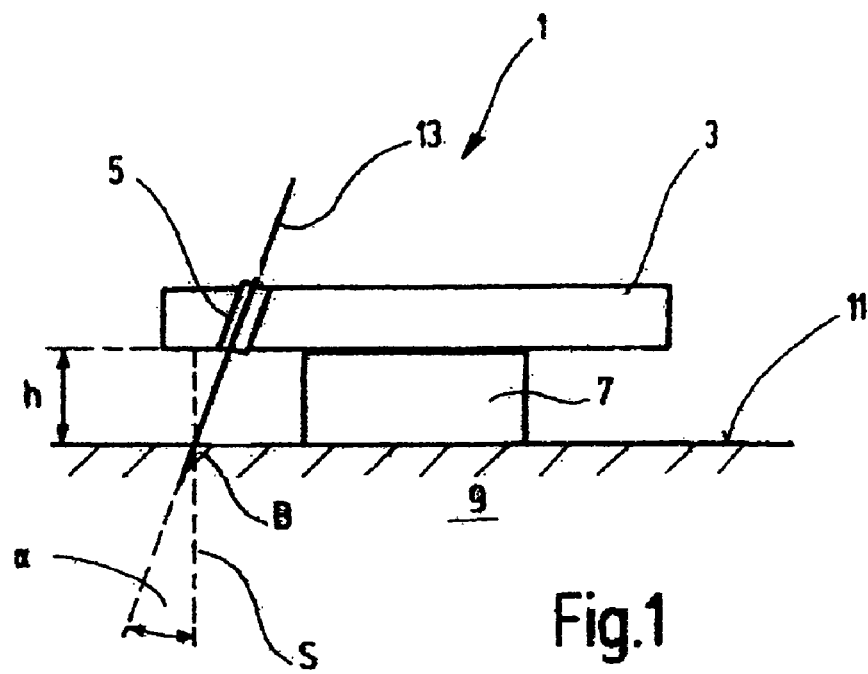
FIG. 1 shows a first illustrative embodiment of a device for controlling the position of bore bushings fitted into a drilling template.

The first illustrative embodiment of a device 1, represented in FIG. 1, has a drilling template 3 with a bore bushing 5 passing through the template which is used to form a drill channel at a desired angle and position in a jaw (not shown) of a patient. The number of bore bushings disposed in the template depends on how many implants the patient is to receive.

The drilling template 3 is held by a holder which is designated hereinafter as reference holder 7 and which is associated with a base 9 of the device 1, in this case placed thereon. The surface of the base 9 forms the measurement plane 11 of the device 1.

A measurement pin 13 is guided through the bore bushing 5 and rests on the measurement plane 11.

It will be seen from FIG. 1 that the bore bushing 5 is arranged at an angle $\alpha$ with respect to an imaginary line S extending perpendicular to the measurement plane 11. Accordingly, the measurement pin 13 extends at the same angle $\alpha$ at which the center axis, coincident with the measurement pin, of the bore bushing 5 extends with respect to the line S.

The reference seat 7 has a defined height h at which the drilling template 3 is held in an intended orientation above the measurement plane 11. The contact point B at which the measurement pin 13 touches the measurement plane 11 is defined by the height h and the angle $\alpha$ of the drilling template 9.

Figure 2:
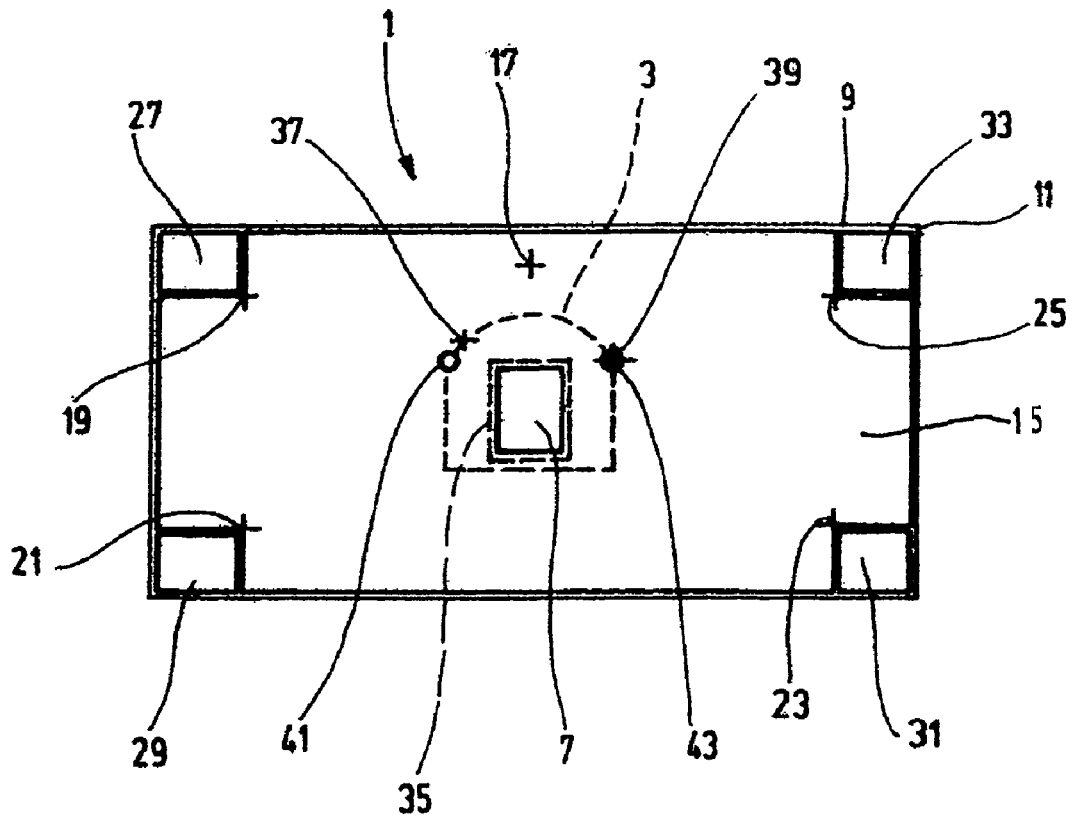
FIG. 2 shows a plan view of a measurement sheet used in conjunction with a device according to FIG. 1.

The device 1 represented in FIG. 1 is shown in a plan view in FIG. 2. For the sake of clarity, the drilling template 3 has been omitted and is indicated only by a broken line.

FIG. 2 shows that the base 9 of the device 1 here has, for example, a substantially rectangular configuration. Accordingly, a rectangular measurement sheet 15 is provided here, which lies on the measurement plane 11.

The measurement sheet 15 is provided with a first marking 17 which indicates at which orientation the drilling template 3 is to be applied to the reference seat 7. For example, the first marking 17 in this case indicates that the drilling template 3 is to be applied to the reference seat 7 in such a way that the part of the drilling template 3 assigned to the front teeth of the patient points in the direction of this marking 17. Naturally, it is also possible to configure the reference seat 7 such that the drilling template 3 can be applied to the reference seat 7 only in the position indicated here.

The measurement sheet 15 lying in the measurement plane 11 is provided with locating points 19, 21, 23 and 25 which are identified by crosses and which are here arranged at a distance from the respective side edges of the measurement sheet 15, in the area of the corners of the latter. Accordingly, the corners of the measurement sheet 15 can be cut out and are thereby able to interact with positioning elements 27, 29, 31, 33 which are arranged on the base 9 or the reference plane 11. The positioning elements can be pin-shaped or, as here, can be rectangular abutment elements which are used to hold the measurement sheet 15 in an exact position on the measurement plane 11. The measurement sheet is provided with a recess 35, which is indicated here by dashed lines and which is of such a size and such a design that the reference seat 7 can engage unimpeded through the measurement sheet 15.

Reference points 37 and 39 identified by crosses are provided on the measurement sheet 15 and are arranged in such a way that they coincide with the contact points B at which the measurement pins 13 touch the measurement sheet 15, when the bore bushings 5 are introduced at the correct angle position into the drilling template 3.

In FIG. 2, circles indicate contact points 41 and 43 at which measurement pins passing through the bore bushings would actually touch the measurement plane 11, that is to say the measurement sheet 15, if a drilling template 3 with bore bushings 6 were applied to the reference seat 7.

It can be clearly seen here in FIG. 2 that the reference point 39 coincides with the contact point 43: the cross of the reference point 39 passes through the imagined center of the contact point 43.

It will also be seen that the reference point 37 and the contact point 41 are arranged at a distance from one another. Such a situation arises when the bore bushing 5 is fitted into the drilling template 3 at a wrong angle, such that the measurement pin 13 does not hit the measurement sheet 15 at the previously calculated site.

The reference points 37 and 39 are calculated with the aid of a program which takes into account the desired orientation of the bore bushings 5 fitted into the drilling template 3, that is to say their angle α, and also the distance h of the drilling template 5 from the measurement plane 11, that is to say the height of the reference seat 7.

The contact points 41 and 43 can be generated by the measurement pins acting with a certain pressure on the measurement sheet 15. However, it is also conceivable to use measurement pins whose tip is designed in such a way that the measurement sheet 15 is perforated in the area of the contact points 41 and 43. The tip can, however, have an ink output, such that the measurement sheet 15 becomes colored in the area of the contact points 41 and 43. For example, it is possible to use ballpoint pen cartridges as measurement pins 13, their external diameter being chosen such that these can be guided through the bore bushings 5.

The illustrative embodiment shown in FIG. 2 can also be modified as follows:

The measurement sheet 15 can also be produced without the cutouts provided at the corners and shown in FIG. 2. For example, transparent tabs can be provided which protrude from the measurement plane 11, engage over the area of the measurement sheet 15 and are provided with markings. These are made congruent with corresponding locating points on the measurement sheet 15 in order to position the latter exactly on the measurement plane 11. This configuration means that the user does not have to form cutouts in the corner areas of the measurement sheet 15.

Correspondingly, it is also possible to dispense with anchoring the reference seat 7 on the measurement plane. Here too, a preferably transparent carrier can be provided which reaches from the edge area of the measurement plane as far as the position at which the reference seat 7 is intended to be positioned. The measurement sheet can then be pushed under the carrier and positioned exactly with the aid of the locating points on the transparent tabs. The carrier described here can of course also be combined with the configuration explained with reference to FIG. 2. The measurement sheet can be pushed under the carrier and oriented by means of the positioning elements, as was explained with reference to FIG. 2.

A particular advantage of this modification is that a measurement sheet 15 can be positioned exactly in the measurement plane 11 without any cutouts, by being pushed under the transparent tabs. As has been stated above, the orientation is effected by bringing locating points on the measurement sheet 15 into congruence with locating points on the tabs. At the same time, the measurement sheet 15 is pushed with the reference seat 7 under the as it were free floating carrier arranged over the measurement plane 11. The carrier is elastic, so that, when the position of the bore bushings 5 is being controlled, it can be easily pressed onto the measurement sheet 15 in order to ensure a defined vertical position relative to the measurement sheet 15.

Figure 3:
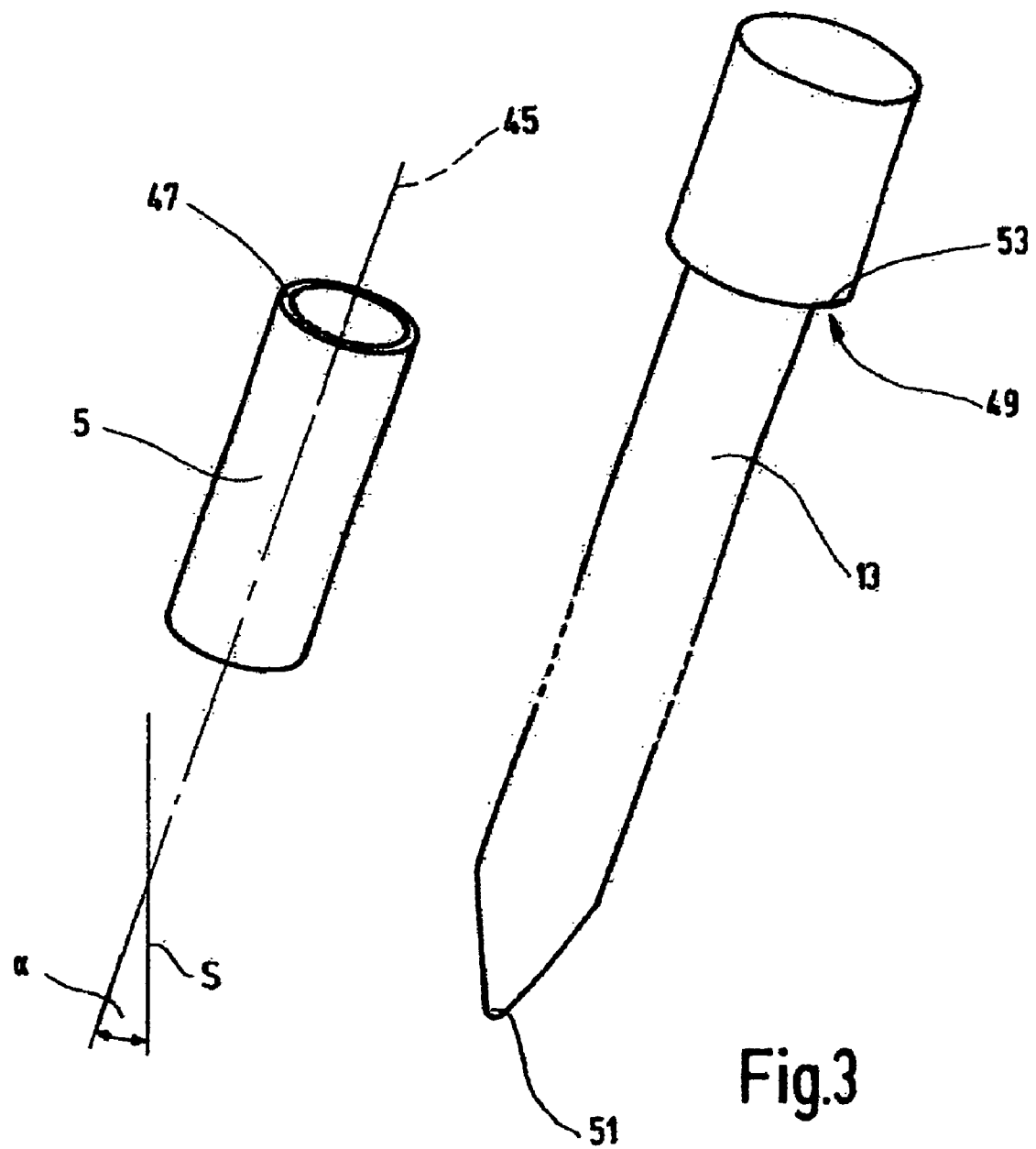
FIG. 3 shows an enlarged representation of a bushing and of a measurement pin.

FIG. 3 shows a bore bushing 5 in isolation and not inserted into a drilling template 3, its center axis 45 being inclined at an angle α with respect to an imaginary line S.

To form holes in a patient's jaw bone, a drill (not shown) whose external diameter is slightly smaller than the internal diameter of the bore bushing 5 is guided through the bore bushing 5. The bushing thus acts as a mechanical guide for the drill, so that the drill penetrates into the patient's jaw bone at a desired angle α. The depth of the drilled hole is defined by the upper edge 47 of the bore bushing 5 serving as an abutment for the drill.

To check the axial positioning of the bore bushing 5 in a drill template 3, the measurement pins 13 mentioned with reference to FIGS. 1 and 2 can be provided with a measurement point 49 which comes to lie exactly in the area of the edge 47 when the measurement pin lies with its tip 51 at the contact point B on the measurement plane 11, that is, on the measurement sheet 15. To make control of the axial position of the bore bushing 5 easier, the measurement point 49 can be designed as a shoulder 53 that is to say configured in such a way that the measurement pin 13 has a greater external diameter above the measurement point 49 than it does below the measurement point. The measurement pin 13 can thus be guided through the bore bushing 5 only as far as the shoulder 53. Should the bore bushing 5 be arranged too far up in the drilling template 3, the measurement pin 13 is not able to touch the measurement plane 11 and thus the measurement sheet 15, with the result that no readable contact point is obtained.

It is therefore easy to tell whether the bore bushing 5 is possibly arranged too high in the drilling template 3, which would mean that a hole formed in the patient's jaw would not be deep enough for an implant.

Conversely, after the measurement pins 13 have been inserted into a bore bushing 5, an observer can easily ascertain whether or not a measurement pin 13 is actually lying with its shoulder 53 on the edge 47 of a bore bushing 5. If a space were to be present here, the bore bushing 5 would be fitted too deep into the drilling template 3, so that the hole formed in the patient's jaw bone would also be too deep and there would be a possible risk to nerve damage or a possibility of perforation of the paranasal sinuses.

FIG. 4 shows a modified illustrative embodiment of a device 10 for controlling the angle position and/or axial position of bore bushings 5 in a drilling template 3, of which bore bushings 5 only the upper edge 47 is indicated here. Measurement pins 13a, 13b and 13c are guided through the bore bushings 5 in order to record the angle position of the bore bushings 5 within the drilling template 3.

When the drilling template 3 is arranged at a predetermined distance above a base (not shown here), the measurement pins 13a, 13b and 13c rest on the base and protrude by a certain length above the drilling template 3, so that their ends are accessible to an observer. It is now possible, in a measurement plane 11, to determine the distance of the ends of the measurement pins from one another or from a reference measurement point not shown here.

The drilling template 3 can be arranged at a certain distance from a base (not shown here) so that the measurement pins 13a, 13b and 13c lie on said base. If the measurement pins are provided with measurement points, these can be compared with the position of the edge 47 of the bore bushings 5 in order to control the axial positioning of the bore bushings. However, it is also possible to use measurement pins with a measurement point 49 which is designed as a shoulder 53, as has been explained with reference to FIG. 3. In this way, the measurement pins can also be inserted into the bore bushings without a base and the distance of their ends can be recorded.

In this illustrative embodiment of the device 10 too, the angle position of the bore bushings can be recorded at a distance from the drilling template 3.

It is additionally possible to check whether the ends of measurement pins provided with a shoulder 53 lie in one plane. Should this be the case, it is possible to infer that the bore bushings 5 lie at a desired depth in the drilling template 3. All that is then needed is to determine the length of the measurement pins remaining above the shoulder 53 in such a way that their ends lie in one plane.

FIG. 5 shows a further illustrative embodiment of a device 100 for controlling the angle position and/or axial position of bore bushings 5 in a drilling template 3.

In the device 100 shown here, a camera 55 is provided which is arranged by means of a suitable holder 57 above a drilling template 3 which is held by a reference seat 7, as has already been explained with reference to FIG. 1. However, it is also conceivable to hold the drilling template 3 by means of a reference seat which is connected to the holder 57 and which is indicated here by a broken line 59. The camera 55 is provided with a computing unit 61 and with a comparison unit 63. A line is indicated here as an example of the connection.

The device 100 is configured in such a way that, instead of the drilling template 3, a test specimen (not shown here) is first held by the reference seat 7 and is recorded by the camera 55. The imaging characteristics can be determined from this recording with the aid of the computing unit 61.

After an image of the test specimen has been recorded, the latter is removed and the drilling template 3 is secured on the reference seat 7. It is now possible for the camera 55 to take an image of the bore bushings 5 fitted in the drilling template 3 and for the arrangement of the bore bushings 5 within the drilling template 3 to be recorded.

Using a program, the actual position of the bore bushings 5 can be compared to the desired position of the bore bushings 5 in the comparison unit 63.

The function of the various devices and the method for controlling the position of bore bushings 5 in drilling templates are discussed in more detail below:

In connection with the device 1 according to FIG. 1, some of the position parameters or derived position parameters are recorded, in this case the angle position and/or axial position of bore bushings 5 in a drilling template 3 with the aid of measurement pins 13. These are guided through the bore bushings 5 until they lie on a measurement plane 11 in which a measurement sheet 15 is arranged. The arrangement of the drilling template 3 and its height h above the measurement plane 11 are determined by a reference seat 7 which defines an exact, predetermined orientation of the drilling template 3 relative to the measurement sheet 15. To determine the position of the bore bushings 5, measurement pins are therefore passed through these, and in this way contact points 41 and 43 are fixed on the measurement sheet 15, either by tips of the measurement pins 13 that perforate or mark the measurement sheet 15, or with the aid of coloring devices with which the measurement pins 13 are equipped.

Reference points 37 and 39 are printed onto the measurement sheet 15 by means of a conventional printer, and also locating points 19, 21, 23 and 25.

By means of the locating points it is possible to exactly predetermine the position of the measurement sheet 15 on the measurement plane 11. When the actual position of the bushings 5 is known, the expected contact points, namely the reference points 37 and 39, can be exactly determined, that is to say calculated in advance, and printed onto the measurement sheet 15.

The measurement pins 13 mark the measurement sheet 15, and a physician can easily tell whether the reference points and contact points coincide with one another. FIG. 2 shows, by way of example, that the reference point 37 and the contact point 41 lie apart, that is to say the bushing, through which a measurement pin was guided, is not arranged in a correct angle position. From the fact that the reference point 39 coincides with the contact point 43, it is readily possible to tell that a correctly oriented bushing 5 is present here.

By means of suitable measurement points 49 on the measurement pins, it is also possible to control the axial positioning of the bore bushings 5: the measurement points 49 have to coincide exactly with the edge 47 of each bore bushing 5. A control can be made particularly easily if the measurement point 49 is realized by a shoulder 53 represented in FIG. 3. If the bushing 5 is arranged too high in the drilling template 3, no contact point can be produced and detected on the measurement sheet 15 when the method is performed. It is thus possible to determine a wrong axial positioning of a bore bushing 5. If the latter were to be inserted too deep in the drilling template 3, the edge 47 of the bore bushing 5 and the measurement point 49 would not coincide. For example, the shoulder 53 would be arranged at a distance from the edge 47. In this case, however, a contact point would be obtained on the measurement sheet 15 possibly indicating a correct angle orientation of the bore bushing 5.

The method carried out by means of the device 1 is characterized in that the desired reference points 37 and 39 can be printed easily on measurement sheets 15 for a wide variety of drilling templates 3. For a physician, it is easy to determine the correct angle position and axial position of one or more bore bushings 5 within a drilling template 3 by guiding measurement pins through bore bushings so that markings, that is to say contact points, are obtained on a measurement plane or on a measurement sheet 15 lying in the measurement plane 11.

By virtue of the fact that the angle position of the bore bushings 5 is determined not directly at the bore bushing but instead at a distance from it, angle deviations of the bore bushings show very clearly, which fact greatly simplifies the control of the correct position of the bore bushings and reliably avoids errors.

The device 10 shown in FIG. 4 permits a method for controlling the position of bore bushings 5 within a drilling template 3, this method also using measurement pins 13a, 13b and 13c which can be pushed into the bore bushings 5. Here, the drilling template 3, as explained with reference to FIG. 1, is arranged over a base. It is then easily possible to measure the ends of the measurement pins lying in a measurement plane 11. It is possible, on the one hand, to measure the distance of the measurement pins from one another or from a reference location, and, on the other hand, to ascertain whether the ends of the measurement pins lie in one plane. This is the case when measurement pins with shoulders 53 are used and the remaining part of the measurement pins measured starting from the shoulder is adapted to the axial position of the bore bushing 5 in the drilling template 3. However, it is also possible, more simply, to provide measurement points 49 on the measurement pins in order to check whether these measurement points 49 coincide with the edge 47 of a bore bushing 5. This measurement is possible if the drilling template 3 is fixed at a defined distance above a base, as has been explained with reference to FIG. 1.

Finally, the method for controlling the position of bore bushings fitted in drilling templates can also be easily carried out using a device 100 which was explained with reference to FIG. 5.

Here too, it is possible to measure the angle position and/or axial position of the bore bushings 5 at a distance from said bore bushings 5. It is therefore not necessary to determine the position of the bore bushings 5 directly on the drilling template 3, something which is not always easy to do, because they are often recessed within the drilling template.

When using the device 100 according to FIG. 5, a test specimen 73 is recorded with the camera 55. When using a known test specimen, it is possible in a first step, with the aid of a computing unit 61, to calculate the imaging characteristics of the camera 55 preferably before each recording of a drilling template. Imaging errors can be eliminated in this way. If less importance is placed on precision, this first step can be omitted if the imaging characteristics of the camera are known.

After the test specimen has been recorded, the drilling template 3 is inserted in its place into the device 100, in which the exact position of one or more bore bushings 5 is to be detected.

With the aid of the camera 55, an image of the drilling template 3 with one or more bore bushings 5 is recorded. The image of the drilling template 3 then lies in the area of the image plane 67 of the camera 55 forming the measurement plane. The image of the drilling template 3 taken by the camera 55 can be compared, using a comparison unit 63, to an image which has been calculated with the aid of a computer from the correct positioning of the bore bushings 5 within the drilling template 3.

Provided the center axis of the bore bushing does not coincide with the optical axis of the camera 55, the upper edge 47 of the bore bushings 5 within the drilling template 3 is not imaged as a circle but as an ellipse. The length of the greater diameter and that of the shorter diameter of the ellipse and the arrangement of the two diameters are determined, on the one hand, by the angle arrangement of a bore bushing and, on the other hand, by how far the latter is displaced in the axial direction within the drilling template 3.

In the comparison unit 63, the recorded values for the diameters of the elliptic image of each bore bushing 5 can be compared to the values obtained from computer calculations. In this way, the actual angle position and/or axial position of each bore bushing within the drilling template can thus be recorded and compared to the desired values.

Figure 6:
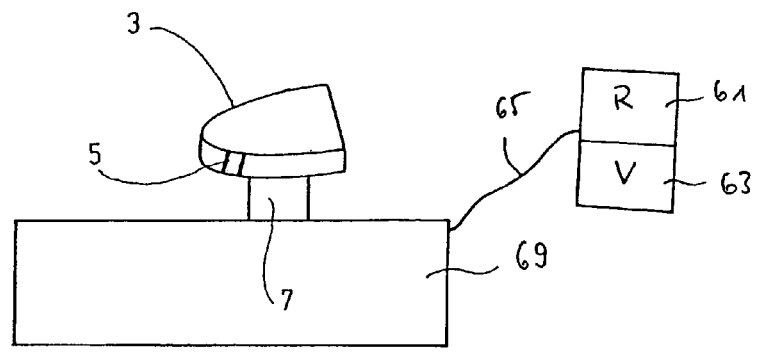
FIG. 6 shows a further illustrative embodiment of the device shown in FIG. 5 utilizing a flatbed scanner.
Figure 7:
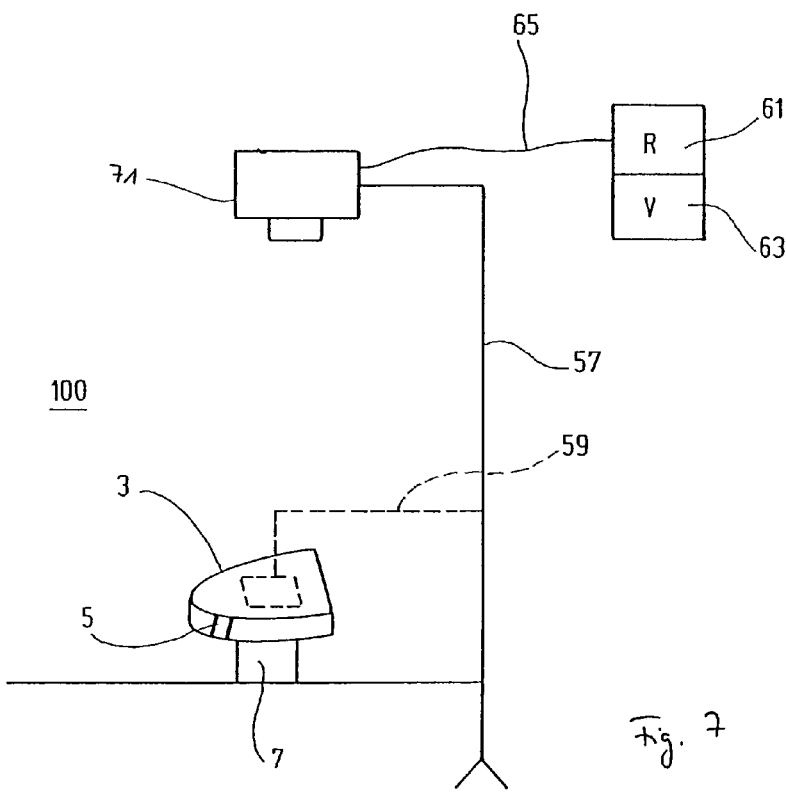
FIG. 7 shows a further illustrative embodiment of the device shown in FIG. 5 utilizing a laser scanner.

Instead of a camera 55, a flatbed scanner 69 (shown in FIG. 6) or a laser scanner 71 (shown in FIG. 7) can also be used.

The following will now therefore be clear:

By means of the various devices shown in FIGS. 1 through 5, and by means of the methods which are described here and which use said devices, it is possible to control the angle position and/or axial position of one or more bore bushings 5 in a drilling template 3. In all cases, the position of the bore bushings is not detected directly on the drilling template, where the bushings are not always easily accessible. The control operation can thus be carried out with great reliability. Since the measurement, in particular of the angle position of the bushings, is carried out at a distance from said bushings, angle errors in particular are reliably detected.

By using measurement pins which are guided through the bore bushings, it is also possible to easily detect the axial position of the bore bushings 5, by using measurement points 49 on the measurement pins, which measurement points 49 are compared with the edge 47 of the bore bushings. It is particularly easy to form the measurement point by means of a shoulder 53 which serves as an abutment and lies on the edge 47 of a bore bushing 5. In this way, the axial position of the bore bushing can also be exactly measured at a distance from said bushing, which simplifies the measurements and the control operation.

The exact positioning of the bushings can also be detected without such measurement pins, specifically, as has been explained with reference to FIG. 5, by using a device 100 which comprises a camera 55. The images of a drilling template 3 recorded by this camera are compared to the images calculated by means of a computer on the basis of X-rays of patients and the planned position of the bore bushing or bore holes. From the elliptical images of the edges 47 of a bore bushing 5, it is possible to determine the axial and angle position of the latter.

In all cases, the result achieved is that the physician does not have to rely on the exact production of a drilling template 3. Instead, he is afforded the possibility of checking and controlling a drilling template before its use in order to determine whether one or more bore bushings 5 in a drilling template 3 have been correctly fitted in the drilling template with respect to their angle position and/or with respect to their axial position. To control the position of the bore bushings 5, it is accordingly sufficient to record only some of the position parameters or derived position parameters of the bore bushings. This simplifies the method, but still leads to increased reliability. The fact that the angle position and/or the axial position of the bore bushings is recorded results in a particularly simple and reliable method. The device described here is additionally characterized by a simple structure.

It should be noted that the method described here for controlling the position of a bore bushing 5 in a drilling template 3, which is generally used in dentistry, is part of a method. The overall method preferably comprises the following steps:

taking an impression of the patient's jaw,
preparing a plaster model,
creating a bite splint with a reference seat 7,
producing a computed tomography (CT) image with bite splint in place, the data obtained from the computed tomography image being used to create a 3D model of the patient's jaw, and the data being stored,
executing a 3D implant plan on a computer,
fitting bore bushings 5 into the bite splint to produce the drilling template 3, the position of the bore bushing 5 here being controlled by the method described with reference to FIGS. 1 to 5,
fitting the bores in the patient's jaw by means of the drilling template 3, preferably drilling the holes in the patient's jaw by drilling with the drill through the bore bushings 5 in the drilling template 3.

The overall system, which performs the overall method, includes both the planning software and also a positioning means which is not the subject of the present application. In particular, the above-described method for controlling the position of the bore bushing 5 in the drilling template 3 is an essential part of the overall method. The advantage of the described method for controlling the position of the bore bushing 5 in the drilling template 3 is that the number of operating steps is reduced compared to conventional methods and the reference marking by the reference points has been simplified. The reference marking by the reference points 37 and 39 is positioned on the measurement plane and thus clearly distinct from the site of the bore bushings 5. An advantage is that the reference marking at the same time also comprises the mechanical plug connection of the reference seat 7 and, therefore, a manual optical calculation and a manual optical orientation is no longer necessary. In this connection, reference is made in particular to FIG. 2 and to the associated figure description which shows the reference points 37 and 39 on the measurement sheet 15 in the measurement plane 11. It is thus clear that the reference seat 7 has a direct relationship to the reference points 37 and 39 and ensures an exact and predetermined orientation of the drilling template 3 relative to the measurement sheet 15.

Particular attention is drawn at this point to the importance of the reference seat 7 which is shown and described with reference to FIGS. 1 and 2 and which in the plaster model, and also in the bite splint, and thus also in the drilling template 3, is always the same reference seat 7. By using this reference seat 7, a reproducible positioning of the drilling template on the measurement plane 11 and on the measurement sheet 15 is ensured. This reference seat 7 likewise ensures the reproducible positioning of the drilling template 3 on a positioning and drilling device with the aid of which the bore bushings 5 are finally fitted into and oriented in the drilling template 3.

The invention claimed is:

1. A method for controlling a position of at least one bore bushing fitted into a drilling template before drilling at least one hole into a patient's jaw bone, the drilling template being located out-side a patient's mouth during the controlling, the controlling comprising:
assigning a measurement plane to a reference seat;
positioning the drilling template with the at least one bore bushing fitted therein on the reference seat such that the drilling template is distanced from the measurement plane and is held at at least one of a predetermined orientation and a predetermined distance with respect to the measurement plane;
measuring or determining an angle position of the at least one bore bushing with respect to a first defined coordinate system or a derived angle position of the at least one bore bushing with respect to a second defined coordinate system, the measuring or determining performed at a distance from the at least one bore bushing by transferring the angle position or the derived position to the measurement plane,
wherein the transferring of the angle position or the derived angle position is performed by guiding a respective measurement pin through the at least one bore bushing,
applying a reference point to the measurement plane, the reference point designating a position at which the respective measurement pin guided through the at least one bore bushing is to meet the measurement plane, when the at least one bore bushing is introduced at the correct angle position into the drilling template; and
contacting the measurement plane with the respective measurement pin and comparing a contact point of the respective measurement pin with the measurement plane to the reference point at the measurement plane.

2. The method as claimed in claim 1, wherein the respective measurement pin includes at least one measurement point to enable determination of an axial position parameter of the at least one bore bushing.

3. The method as claimed in claim 2, further comprising checking whether the respective measurement pin guided through the at least one bore bushing touches the measurement plane to enable determination of an axial position parameter of the at least one bore bushing.

4. The method as claimed in claim 1, wherein a plurality of reference points are generated by a printer.

5. The method as claimed in claim 1, further comprising placing the measurement plane in an image plane of a camera.

6. The method as claimed in claim 5, further comprising:
positioning a test specimen on the reference seat and recording the specimen with the camera; and
calculating imaging characteristics of the camera using a computing unit.

7. The method as claimed in claim 5, further comprising calculating a desired position of the at least one bore bushing.

8. The method as claimed in claim 1, further comprising positioning a test specimen on the reference seat and recording the specimen with at least one of a flatbed and a laser scanner; and calculating imaging characteristics of the respective one of the flatbed and the laser scanner using a computing unit.

9. The method as claimed in claim 8, further comprising calculating a desired position of the at least one bore bushing.

10. The method as claimed in claim 9, further comprising positioning the drilling template on the reference seat, recording a position of the drilling template, and comparing an actual position of the at least one bore bushing with the desired position of the at least one bore bushing using a comparison unit.

11. The method as claimed in claim 1, wherein the controlling further comprises measuring or determining an axial position or derived axial position of the at least one bore bushing.

12. A method for controlling a position of at least one bore bushing fitted into a drilling template before drilling at least one hole into a patient's jaw bone, the drilling template being located out-side a patient's mouth during the controlling, the controlling comprising:
assigning a measurement plane to a reference seat;
positioning the drilling template with the at least one bore bushing fitted therein on the reference seat such that the drilling template is distanced from the measurement plane and is held at at least one of a predetermined orientation and a predetermined distance with respect to the measurement plane;
measuring or determining an angle position of the at least one bore bushing with respect to a first defined coordinate system or a derived angle position of the at least one bore bushing with respect to a second defined coordinate system, the measuring or determining performed at a distance from the at least one bore bushing by transferring the angle position or the derived position to the measurement plane,
wherein the transferring of the angle position or the derived angle position is performed by guiding a respective measurement pin through the at least one bore bushing, and
applying a reference point to the measurement plane, the reference point designating a position at which the respective measurement pin guided through the at least one bore bushing is to meet the measurement plane, when the at least one bore bushing is introduced at the correct angle position into the drilling template,
wherein a plurality of reference points are predetermined on a measurement sheet.

13. The method as claimed in claim 12, wherein the measurement sheet includes locating points.

14. The method as claimed in claim 13, further comprising assigning position elements to the locating points.

15. The method as claimed in claim 12, wherein the controlling further comprises measuring or determining an axial position or derived axial position of the at least one bore bushing.

16. A method for controlling a position of at least one bore bushing fitted into a drilling template before drilling at least one hole into a patient's jaw bone, the drilling template being located out-side a patient's mouth during the controlling, the controlling comprising:
assigning a measurement plane to a reference seat;
positioning the drilling template with the at least one bore bushing fitted therein on the reference seat such that the drilling template is distanced from the measurement plane and is held at at least one of a predetermined orientation and a predetermined distance with respect to the measurement plane;
measuring or determining an angle position of the at least one bore bushing with respect to a first defined coordinate system or a derived angle position of the at least one bore bushing with respect to a second defined coordinate system, the measuring or determining performed at a distance from the at least one bore bushing by transferring the angle position or the derived position to the measurement plane, wherein the transferring of the angle position or the derived angle position is performed by guiding a respective measurement pin through the at least one bore bushing, and guiding respective measurement pins through a plurality of bore bushings fitted into the drilling template, and, when the measurement pins are inserted into the bore bushings, measuring at least one of a distance of the ends of the measurement pins from one another and a distance of each end of a respective measurement pin from a corresponding reference point in the measurement plane.

17. The method as claimed in claim 16, wherein each of the measurement pins has at least one of a predefined length and a measurement point to enable determination of an axial position parameter of the at least one bore bushing.

18. The method as claimed in claim 17, wherein measuring of at least one of a distance of the ends of the measurement pins from one another and a distance of each end of a respective measurement pin from a corresponding reference point at the measurement plane is performed only for measurement pins having ends or measurement points laying at the measurement plane.

19. The method as claimed in claim 16, wherein the controlling further comprises measuring or determining an axial position or derived axial position of the at least one bore bushing.

* * * * *

UNITED STATES PATENT AND TRADEMARK OFFICE
CERTIFICATE OF CORRECTION

PATENT NO. : 8,382,475 B2  
APPLICATION NO. : 10/547108  
DATED : February 26, 2013  
INVENTOR(S) : Wolfram Stein et al.

Page 1 of 1

It is certified that error appears in the above-identified patent and that said Letters Patent is hereby corrected as shown below:

Title Page, Item (75) Inventors should read:

(75) Inventors: Wolfram Stein, Heidelberg (DE);
Florian Schober, Zurich (CH);
Leonhard Blümcke, Graben-Neudorf (DE)

Signed and Sealed this  
Fourth Day of June, 2013

Teresa Stanek Rea  
*Acting Director of the United States Patent and Trademark Office*

UNITED STATES PATENT AND TRADEMARK OFFICE
CERTIFICATE OF CORRECTION

PATENT NO.       : 8,382,475 B2
APPLICATION NO. : 10/547108
DATED            : February 26, 2013
INVENTOR(S)      : Stein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1212 days.

Signed and Sealed this
First Day of September, 2015

Michelle K. Lee
*Director of the United States Patent and Trademark Office*